(12) United States Patent  
Nemoto (10) Patent No.: US 7,316,171 B2  
(45) Date of Patent: Jan. 8, 2008

(54) BIOSIGNAL INTENSITY MEASURING METHOD, BEDDING STATE JUDGING METHOD, AND BEDDING STATE MONITORING DEVICE

(75) Inventor: Shin Nemoto, Kashiwa (JP)

(73) Assignee: CB System Co., Tokyo (JP)

( * ) Notice: Subject to any disclaimer, the term of this patent is extended or adjusted under 35 U.S.C. 154(b) by 264 days.

(21) Appl. No.: 10/532,246

(22) PCT Filed: Nov. 5, 2003

(86) PCT No.: PCT/JP03/14087

§ 371 (c)(1),  
(2), (4) Date: Apr. 22, 2005

(87) PCT Pub. No.: WO2004/043248

PCT Pub. Date: May 27, 2004

(65) Prior Publication Data

US 2006/0042409 A1    Mar. 2, 2006

(30) Foreign Application Priority Data

Nov. 7, 2002    (JP) ............................. 2002-358712

(51) Int. Cl.  
    *A61B 5/00*    (2006.01)  
    *A61B 5/103*   (2006.01)  
    *A61B 5/11*    (2006.01)  
    *G08B 21/04*   (2006.01)  
    *G08B 23/00*   (2006.01)

(52) U.S. Cl. .................... 73/866.1; 73/865.4; 600/534; 600/587; 600/595

(58) Field of Classification Search ............... 73/866.1, 73/865.4; 340/575; 600/534, 587, 595  
See application file for complete search history.

(56) References Cited

U.S. PATENT DOCUMENTS 5,479,939 A * 1/1996 Ogino ........................ 600/595

FOREIGN PATENT DOCUMENTS

| JP | A 05-192315 | 8/1993 |
| JP | 8-131407 A * | 5/1996 |
| JP | A 11-019056 | 1/1999 |
| JP | A 2002-052010 | 2/2002 |
| JP | A 2002-058653 | 2/2002 |
| JP | A 2004-130012 | 4/2004 |

* cited by examiner

*Primary Examiner*—Daniel S. Larkin  
(74) *Attorney, Agent, or Firm*—Oliff & Berridge, PLC.

(57) ABSTRACT

A person who is elderly, requires care, or an inpatient who is under the care by his or her family members, a nursing care worker, or a nurse in a hospital or medical institution must be monitored constantly, however the caregiver cannot be in attendance on the patient all the time. A biosignal intensity measuring method is provided to solve the above problem. According to the measuring method, output signals from a noninvasive sensor, which detects biosignals from a lying subject, are amplified and noises other than the biosignals are attenuated via a signal amplifying/shaping unit, and the amplified signals are controlled by an automatic gain control (AGC) unit to have sizes within a prescribed range, then parameters acquired by signal gains in a control circuit upon carrying out automatic gain control are output as the output signal intensity of the biosignals to calculate biosignal intensity. A bedding state monitoring method is also provided. According to the monitoring method, the calculated signal intensity is used to monitor the bedding state of the subject, such as a state of being in or out of bed, of weakening or stoppage of biosignals, of body motion, or the like.

20 Claims, 7 Drawing Sheets

BIOSIGNAL INTENSITY MEASURING METHOD, BEDDING STATE JUDGING METHOD, AND BEDDING STATE MONITORING DEVICE

This application is the U.S. National Stage of PCT/JP2003/014087, filed Nov. 5, 2003, which claims priority from Japanese Patent Application No. 2002-358712 filed Nov. 7, 2002, the disclosures of both of which are incorporated herein in their entireties by reference thereto.

BACKGROUND

The disclosure relates in general to a biosignal intensity detecting method, a bedding state judging method, and a bedding state monitoring device. The methods and monitoring device are used to detect whether a target person is in or out of bed or bedclothes and whether the intensity level of biosignals from the person in bed is decreasing.

An elderly person, a person who requires care, or an inpatient is under the care of his or her family members, a nursing care worker, or a nurse in a hospital or a medical institution who must pay constant attention to the condition of their patient or elderly person but cannot be in attendance all the time.

For example, when a family lives with an elderly person who requires care, someone in the family must go to the elderly person's room frequently to check the condition or behavior of the elderly person. In a nursing-care institution or hospital, patrolling at night on a regular basis is required for checking the condition of a patient during nighttime. But under present circumstances it is difficult to find people to spare for patrolling. Additionally, in the case where an accident happens to a patient, there is no other way for the patient but to use a buzzer attached to a bed to contact hospital personnel. The buzzer is useless if the patient is in no condition to operate the buzzer. An elderly person living alone is at an even greater disadvantage. The elderly person has no attendants to take care of him or her, so others cannot know about his or her condition.

If an elderly person or patient in bed has an abnormality in his or her body and is left alone for a long time, he or she may be placed in a fatal condition. Hence a monitoring device, capable of constantly monitoring the condition and daily behavior of a patient, has been in great demand.

It is desirable to monitor the condition of a patient without imposing any mental or physical burden on the patient. For this reason, a device for noninvasive monitoring is imperative for monitoring the patient.

The inventor has proposed a novel method disclosed in Japanese Published Unexamined Patent Application No. H11-19056. According to the method, an air mat is laid under a subject and a minute differential pressure sensor for detecting the inner pressure of the mat is used to detect vibrations caused by the heartbeat of the subject in a noninvasive manner. The vibrations are processed as signals, which are detected as heartbeat signals or respiratory signals.

The inventor has also proposed an apparatus disclosed in Japanese Published Unexamined Patent Application No. 2002-58653. According to the apparatus, an air tube is laid under a subject and a minute differential pressure sensor for detecting the inner pressure of the air tube is used to detect vibrations caused by the heartbeat of the subject in a noninvasive manner. The vibrations are processed as signals, which are detected as heartbeat signals or respiratory signals.

In addition, a method for judging whether a person is in bed is disclosed in Japanese Published Unexamined Patent Application No. H5-192315. According to the method, an air mat is laid under the bed or bedclothes, and a pressure change of the air mat caused by the person's body motion, tossing, etc., is detected to make a judgment whether a person is in or out of bed.

The method disclosed in Japanese Published Unexamined Patent Application No. H5-192315 allows a monitoring person to know whether the subject is in or out of bed, but does not allow the monitoring person to know the condition or daily behavior of the subject.

SUMMARY

The inventor has disclosed in Japanese Published Unexamined Patent Application No. H11-19056 and Japanese Published Unexamined Patent Application No. 2002-58653, described above, methods for extracting heartbeat signals and respiratory signals, for use in the detection of microsignals. Detecting microsignals takes a great effort, and a temporary failure in detecting the signals may occur when an excessive large signal caused by the subject's tossing is generated. The methods, therefore, have a problem in terms of continuity in detection.

In order to solve the above mentioned problems, an object is to provide a biosignal detecting method, a bedding state judging method, and a bedding state monitor, which make it possible to detect the intensity of microsignals continuously and enable a judgment whether a subject is in or out of bed.

A first aspect is a biosignal measuring (detecting) method. Output signals from a noninvasive sensor, which detects biosignals from a lying subject, are amplified and attenuated with respect to noises other than the biosignals via a signal amplifying/shaping means. The biosignals are controlled by an automatic gain control (AGC) means to have sizes within a prescribed range, and parameters acquired by signal gains in a control circuit upon carrying out automatic gain control are output as the output signal intensity of the controlled signals to calculate biosignal intensity.

A second aspect is, in the biosignal measuring method, the signal amplifying/shaping means has an amplifying characteristic that reduces the signal level of heartbeat signals and pulse signals in a bandwidth other than the main bandwidth of the signals.

A third aspect is, in the biosignal measuring method, the signal amplifying/shaping means has a band-pass filter that reduces the signal level of heartbeat signals and pulse signals in a bandwidth other than the main bandwidth of the signals.

A fourth aspect is, in the biosignal measuring method, when the size of the output from the noninvasive sensor exceeds a prescribed range for more than a certain time, a judgment is made that a subject is making body motion.

A fifth aspect is a bedding state judging method. The output signals from the noninvasive sensor, which detects biosignals from a lying subject, are amplified and attenuated with respect to the noises other than the biosignals via the signal amplifying/shaping means. The amplified signals are controlled by the automatic gain control (AGC) means to have sizes within a prescribed range, and the parameters acquired by signal gains in the control circuit, upon carrying out automatic gain control, are calculated as the output signal intensity of the controlled signals. The calculated signal intensity is used to monitor the bedding state of the subject, such as a state of being in or out of bed, of weakening or stoppage of biosignals, of making body motion, or the like.

A sixth aspect is, in the bedding state judging method, the signal amplifying/shaping means has the amplifying characteristic that reduces the signal level of heartbeat signals and pulse signals in a bandwidth other than the main bandwidth of the signals.

A seventh aspect is, in the bedding state judging method, the signal amplifying/shaping means has the band-pass filter that reduces the signal level of heartbeat signals and pulse signals in a bandwidth other than the main bandwidth of the signals.

An eighth aspect of the invention is, in a bedding state monitor, which includes the noninvasive sensor that detects biosignals and the body motion of a lying subject, the signal amplifying/shaping means that attenuates the noises other than the biosignals included in the output signals from the noninvasive sensor, a non-bedding detecting sensor for confirming the subject's being out of bed, the automatic gain control means that controls signals given by eliminating noises from the output signals from the noninvasive sensor via the signal amplifying/shaping means so that the signals have sizes within a prescribed range, the signal intensity calculating means that calculates the parameters acquired by signal gains in the control circuit upon carrying out automatic gain control as the output signal intensity of the biosignals, and a bedding state judging means that makes a judgment on the subject's being in or out of bed, weakening or stoppage of biosignals, or the like, using a plurality of the signal intensities or parameters calculated from the signal intensities.

A ninth aspect is, in the bedding state monitor, the signal amplifying/shaping means has the amplifying characteristic that reduces the signal level of heartbeat signals and pulse signals in a bandwidth other than the main bandwidth of the signals.

A tenth aspect is, in the bedding state monitor, the signal amplifying/shaping means has the band-pass filter that reduces the signal level of heartbeat signals and pulse signals in a bandwidth other than the main bandwidth of the signals.

An eleventh aspect is, in the bedding state monitor, a body motion detecting means that detects body motion from the output of the noninvasive sensor, and the bedding state judging means monitors the occurrence of the body motion using output from the body motion detecting means.

A twelfth aspect is, in the bedding state monitor, the body motion detecting means judges that a subject is making body motion when the size of output from the noninvasive sensor exceeds a prescribed range for more than a certain time.

A thirteenth aspect is, in the bedding state monitor, the noninvasive sensor comprises a capacitor microphone for detecting micropressure, and a hollow, elastic tube or a hollow, elastic tube with an inserted core wire thinner than the hollowed part of the tube, the tube being connected to the microphone.

A fourteenth aspect is, in the bedding state monitor, the non-bedding detecting sensor is a sensor for detecting weight.

A fifteenth aspect is, in the bedding state monitor, the non-bedding detecting sensor is an infrared sensor.

BRIEF DESCRIPTION OF THE DRAWINGS

The invention will be described with reference to the drawings, in which.

DETAILED DESCRIPTION OF EMBODIMENTS

Figures 1A, 1B:
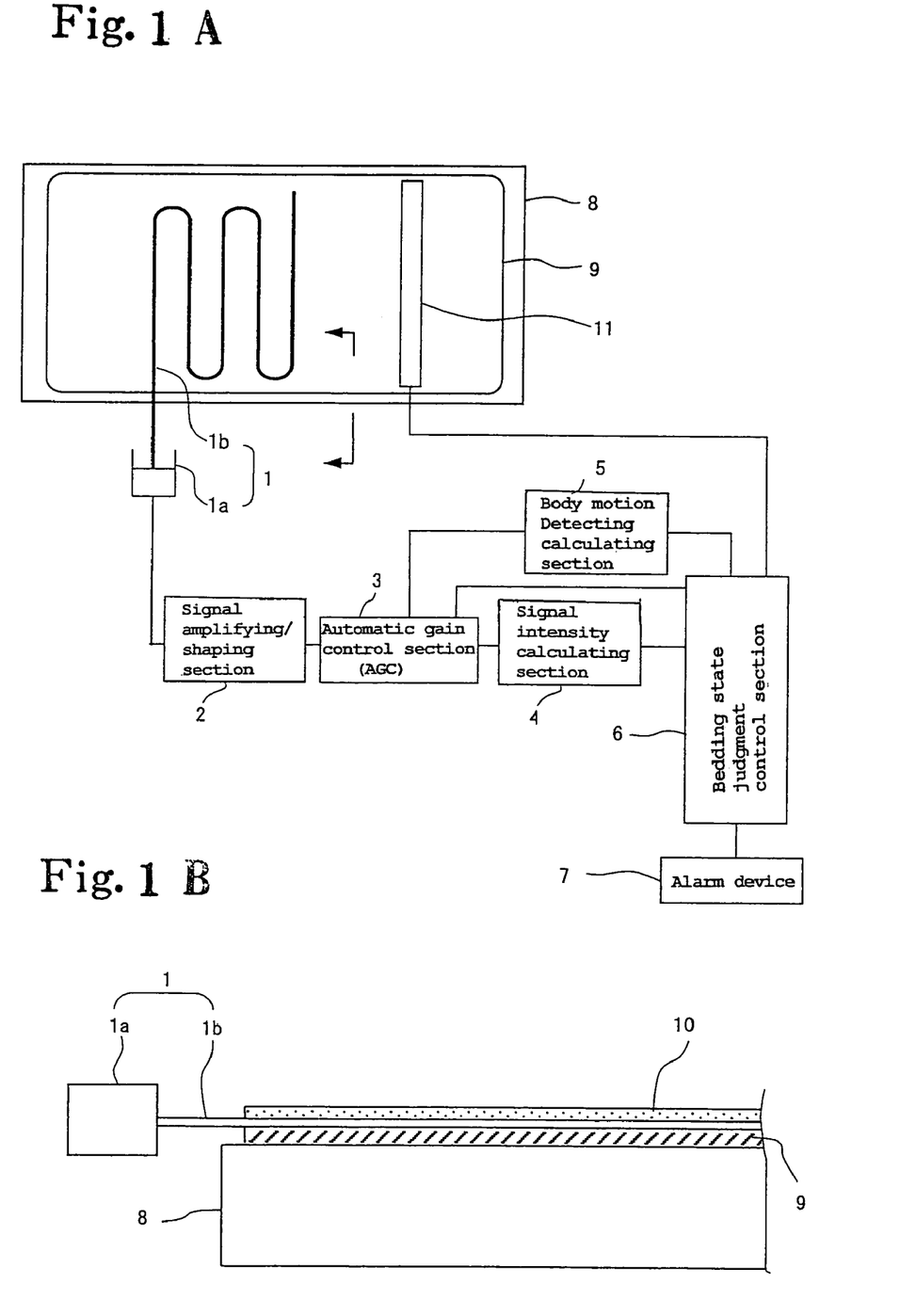
FIGS. 1A and 1B are block diagrams for depicting the flow of a procedure for detecting signals from a subject in a noninvasive manner and detecting biosignals using the detected signals.

FIGS. 1A and 1B are the block diagrams depicting the flow of the procedure for detecting biosignals in a noninvasive manner, calculating the intensity of the biosignals, and making a judgment on the presence or absence of the biosignals and a bedding state, such as being in or out of bed, using the biosignal intensity output, according to an exemplary embodiment. FIG. 1B is a partial sectional view of FIG. 1A in the direction viewed from the arrow.

A noninvasive sensor 1 comprises a minute differential pressure sensor 1a and a pressure detecting tube 1b, and is arranged on a bed 8. As shown in FIGS. 1A and 1B, the pressure detecting tube 1b is folded back and forth several times to extend over a large portion of the bed to secure ample space for detecting pressure.

The pressure detecting tube 1b is placed on a hard sheet 9 spread on the bed 8, as shown in FIGS. 1A and 1B. The hard sheet 9 is covered with an elastic cushion sheet 10, which is further covered with bedclothes (a "futon" in Japanese, not shown in the drawings), on which a subject is laid. The pressure detecting tube 1b may be incorporated into the cushion sheet 10 to stabilize the position of the pressure detecting tube 1b.

The minute differential pressure sensor 1a detects the fluctuation of micropressure, and is of a capacitor microphone type for low frequency according to this exemplary embodiment. The minute differential pressure sensor 1a of this type, however, can be replaced with another type if the replaced type has a proper resolution and a dynamic range.

While an acoustic microphone, in general use, has a structure showing less sensitivity to a low-frequency region, the capacitor microphone for low frequency used for the embodiment is provided with a chamber formed behind a pressure-receiving surface, which improves the characteristics of the capacitor microphone for the low-frequency region. This makes the capacitor microphone applicable to the detection of the fluctuation of micropressure in the pressure detecting tube 1b. The capacitor microphone is also superior in measuring minute differential pressure, having a resolution of 0.2 Pa (pascal) and a dynamic range of approximately 50 Pa to exert a capability several times as high as a conventional minute differential pressure sensor using ceramics. The capacitor microphone, therefore, is suitable for detecting micropressure applied to the pressure detecting tube 1b via biosignals transmitted through the body surface of a subject. The frequency characteristics of the capacitor microphone are almost flat in a range from 0.1 Hz to 30 Hz (hertz), which is another factor for making the capacitor microphone appropriate to the detection of minute biosignals, such as heart rate, breathing rate, pulse, very small body movements or the like.

The pressure detecting tube 1*b*, which functions as a pressure detecting section in the noninvasive sensor 1, must have proper elasticity so that the inner pressure of the pressure detecting tube 1*b* changes in response to the fluctuation range of pressure caused by the biosignals. Also, the capacity of a hollowed part in the tube 1*b* should be selected properly so that a pressure change inside the tube 1*b* is transmitted to the minute differential pressure sensor 1*a* at a proper response speed. When the pressure detecting tube 1*b* cannot have the proper elasticity and hollowed part capacity simultaneously, a core wire of proper thickness may be inserted into the hollowed part and extended along the entire length of the tube 1*b* to secure the proper capacity for the hollowed part. Inserting the core wire of the proper thickness into the pressure detecting tube 1*b* also prevents such trouble that the tube 1*b* is completely crushed and becomes unable to transmit the pressure change to the minute differential pressure sensor 1*a*.

A non-bedding detecting sensor 11 is a sensor for helping to see if a subject is out of a bed 8. FIG. 1A shows, as an example of the sensor 11, that a tape switch is stretched across the whole length of the bed 8. The tape switch is turned on when the subject's body is on the switch, and turned off when the body is removed.

Figure 2:
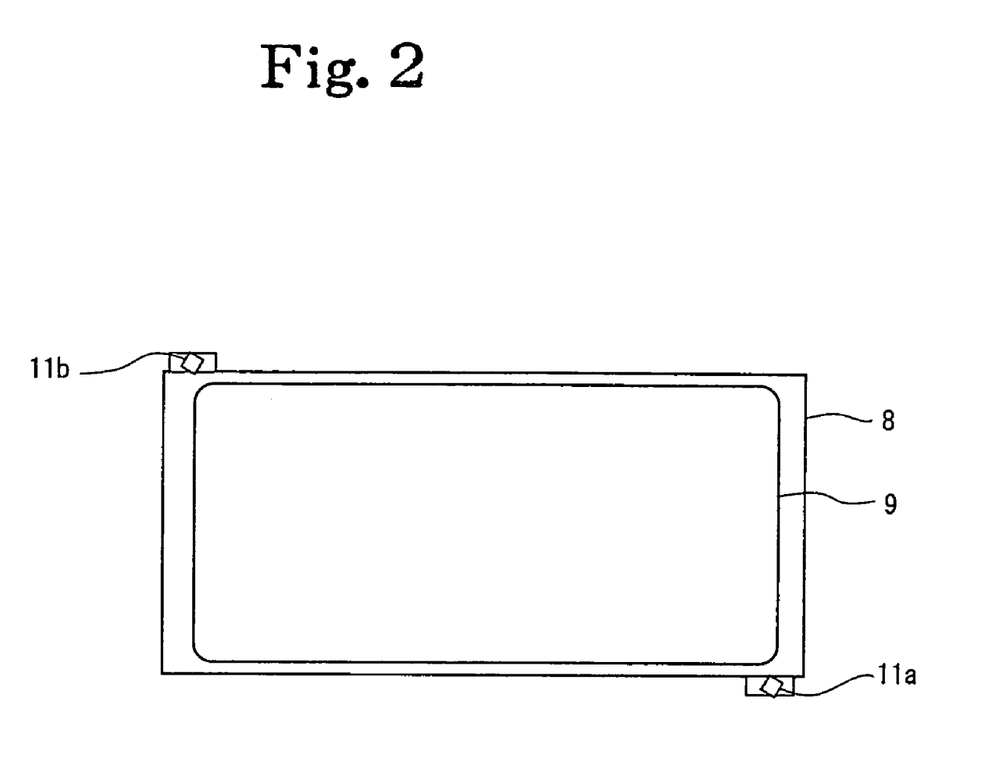
FIG. 2 is a plan view of another embodiment of the non-bedding detecting sensor.

FIG. 2 is an example where an infrared sensor is used as the non-bedding detecting sensor 11. The infrared sensor comprises an emitting part 11*a* and a light-receiving part 11*b*, and they are in an arrangement where infrared rays emitted from the emitting part 11*a* are received by the light-receiving part 11*b*. The infrared sensor is switched on when the subject lies on the bed and switched off when the subject is out of the bed.

Figure 3:
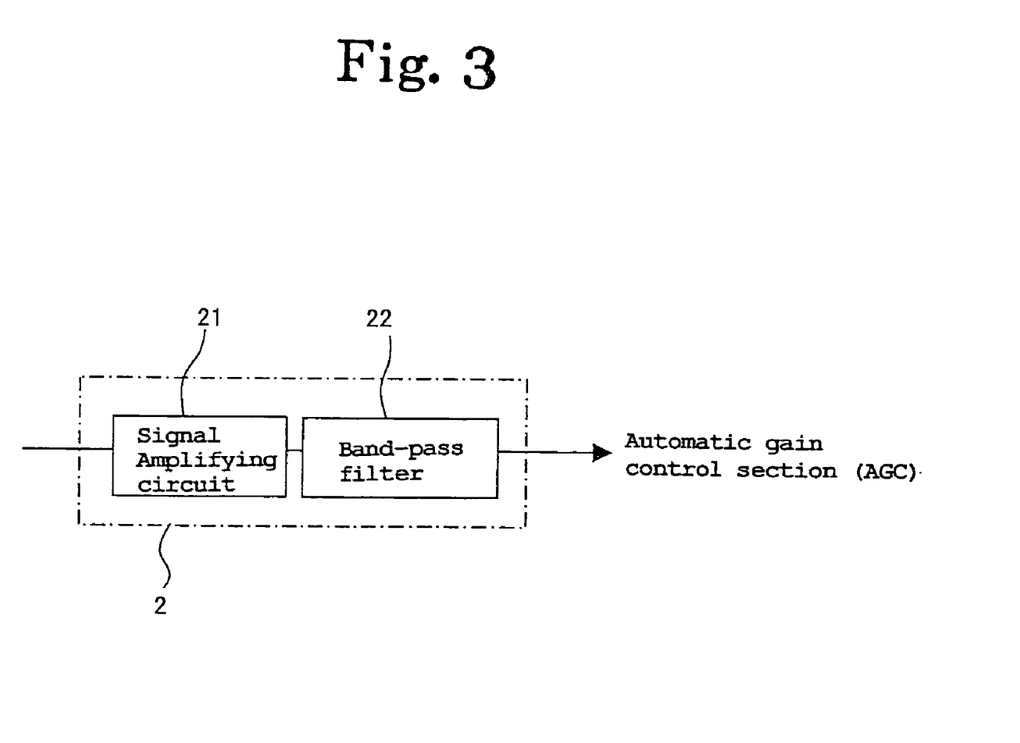
FIG. 3 is a block diagram depicting the details of the signal amplifying/shaping section.

FIG. 3 is the block diagram that depicts the details of a signal amplifying/shaping section 2, which has a function of amplifying signals output from the noninvasive sensor 1 while attenuating noises other than biosignals included in the output signals. As shown in FIG. 3, the signal amplifying/shaping section 2 comprises a signal amplifying circuit 21 and a band-pass filter 22. The signal amplifying circuit 21 amplifies output signals from the noninvasive sensor 1 and the band-pass filter 22 passes only the signals that have frequencies required for measuring the intensity of biosignals out of the output signals. According to this exemplary embodiment, the band-pass filter 22 is given a preset filtering function that passes signals having frequencies ranging from approximately 7 Hz to 30 Hz and attenuates the signals in the frequency bandwidth other than 7 Hz to 30 Hz.

Signals caused by the subject include heartbeat signals, pulse signals, respiratory signals, and signals generated by body motions, such as tossing. The heartbeat signals appear in a frequency bandwidth of 10 Hz to 20 Hz, while the pulse signals in a frequency bandwidth of 0.8 Hz to 1.5 Hz, and the respiratory signals in a frequency bandwidth of 0.2 Hz to 0.4 Hz. Meanwhile, noises, which are not caused by the subject, include noises due to wind, which appear as signals having frequencies of around 1 Hz, noises due to emissions from a fluorescent lamp, appearing as signals of 50 Hz to 60 Hz, low-frequency noises due to voices, appearing as signals of more than 300 Hz, and low-frequency noises from a construction site or factory, appearing as signals of 20 Hz to 300 Hz.

When the passing band of the signal amplifying/shaping section 2 is set within the range of 7 Hz to 30 Hz as in the exemplary embodiment, most noises not caused by the subject can be attenuated, and the passed heartbeat signals and pulse signals are sent to an automatic gain control section 3. Although the respiratory signals are cut off, the presence or absence of biosignals can be confirmed without the respiratory signals, as the respiratory signals are sometimes discontinued when a non-breathing time occurs, so that the above passing band setting presents no trouble in measuring the intensity of biosignals.

The band-pass filter 22 can be eliminated from the signal amplifying/shaping section 2 when the signal amplifying circuit 21 is given the characteristics that amplify signals in the main frequency band of biosignals and attenuates signals in the frequency band of noises. It is also applicable that the signal amplifying circuit 21 is set to pass signals in the main frequency band and the band-pass filter 22 is provided to further attenuate noise elements.

Figure 6:
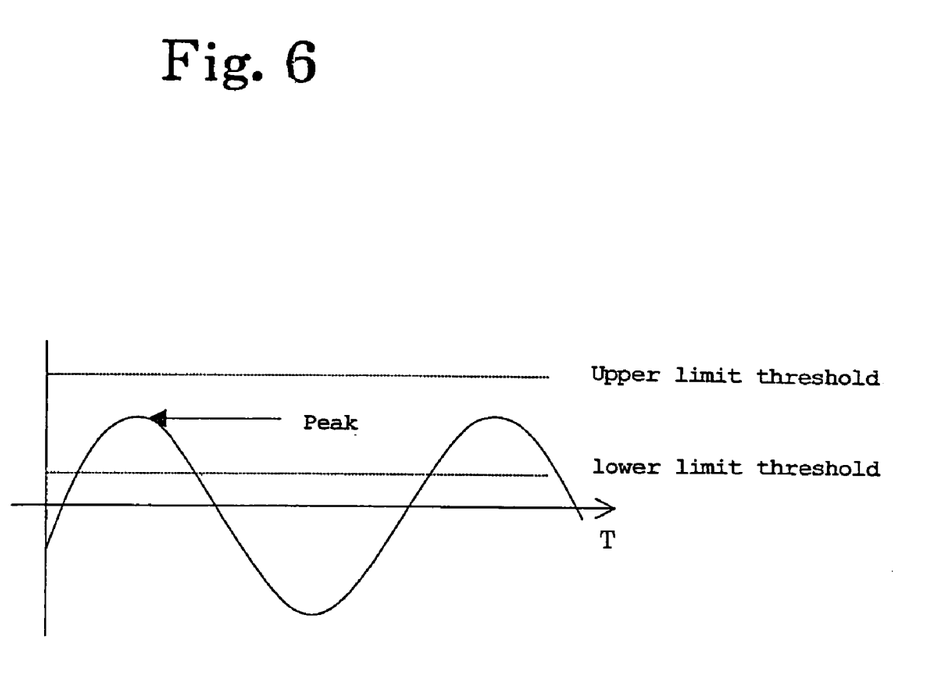
FIG. 6 is an explanatory drawing for explaining a method for setting a gain in the AGC circuit.

The automatic gain control section 3 is composed of an automatic gain control (AGC) circuit, through which the gain of output from the signal amplifying/shaping section 2 is automatically controlled so that the output is processed into signals within a prescribed level. The gain resulting from the gain control is sent to a signal intensity calculating section 4. In this exemplary embodiment, the gain of output signals is set so that the amplitude of the signals is reduced when the peak of the signals surpasses an upper limit threshold while being increased when the peak drops below a lower limit threshold, as shown in FIG. 6. Respective output signals processed into the prescribed level are sent to a bedding state judgment control section 6.

The signal intensity calculating section 4 calculates the intensity of the signals, using the gain resulting from the gain control on the output from the noninvasive sensor 1 and the environmental noise sensor 2 at the automatic gain control section 3.

Because the gain given by the AGC circuit is small when the signals are large and is large when the signals are small, a function that represents signal intensity in inverse proportion to the gain is required in order to represent signal intensity using the gain.

On the other hand, when output from the noninvasive sensor 1 repeatedly surpasses the upper limit of the automatic gain control in a prescribed time, it is assumed that the subject's body is in motion, such as tossing or turning. A body motion detecting/calculating section 5 monitors such a time, during which output from the noninvasive sensor 1 surpasses the upper limit, and detects the body motion.

The bedding state judgment control section 6 is a judgment section that makes a judgment on the presence or absence of biosignals and the subject's being in or out of bed on the basis of output from the signal intensity calculating section 4, the body motion detecting/calculating section 5, and the non-bedding detecting sensor 11.

Next, a method for measuring the biosignal intensity and for making judgments on the presence or absence of biosignals and the subject's being in or out of bed are described.

According to the exemplary embodiment, biosignals are detected by detecting a pressure change in the pressure detecting tube 1*b* arranged under the lying subject. Because of this, vibrations not caused by the subject and transmitted to bedclothes, such as vibrations caused by wind or voices, steps of people other than the subject in a room, by traffic, construction, or factory operation, etc., may also be applied to the pressure detecting tube 1*b* as additional signals, which makes it impossible to detect the accurate intensity of biosignals.

Thus, according to the method for measuring biosignal intensity, the above problem is solved by attenuating signals caused by vibrations other than the subject, which are included in output signals from the noninvasive sensor 1 for detecting biosignals, at the signal amplifying/shaping section 2 and calculating the accurate intensity of biosignals at the biosignal intensity calculating section 4. The signal amplifying/shaping section 2 is set to attenuate signals in a bandwidth other than that ranging from 7 Hz to 30 Hz. A bandwidth set for attenuation, however, is not limited to the above bandwidth, and its range may be changed if the intensity of biosignals can be measured after all.

A biosignal intensity F is calculated at the biosignal intensity calculating section 4 using the following equation (A):

$$F = Aa - Aa_0 \qquad (A)$$

where Aa is the transfer average of the intensity of signals from the noninvasive sensor 1 in a certain time, while $Aa_0$ is that of the intensity of signals from the noninvasive sensor 1 in a second when no load is applied on the noninvasive sensor 1. $Aa_0$ is measured at initial setting and the absence of the subject to use the latest value. The value of the biosignal intensity F is a maximum at F (100), and F (50) indicates 50% intensity of F (100).

Figure 4:
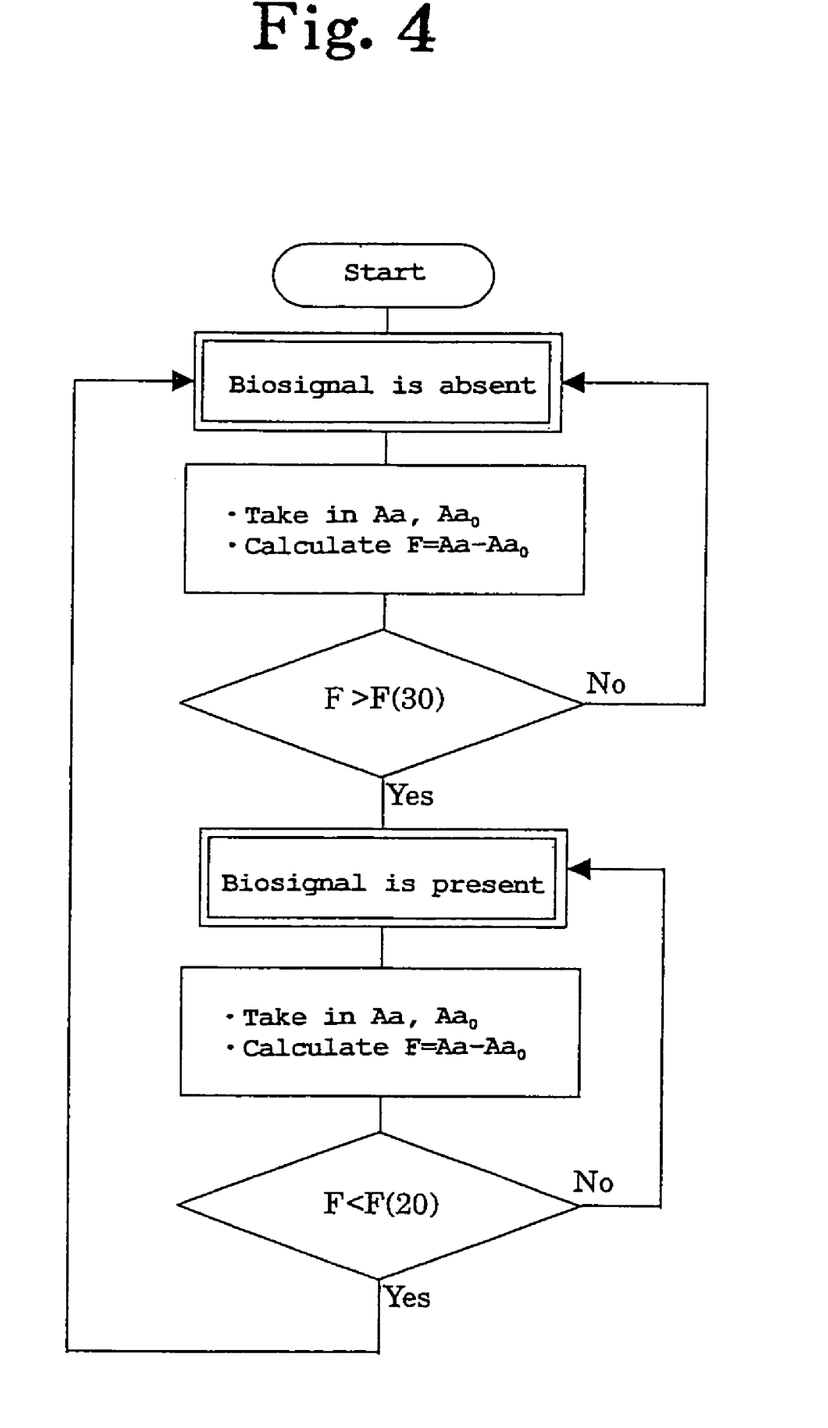
FIG. 4 is a flowchart of a procedure for judging the presence or absence of biosignals.

FIG. 4 is the flowchart of an example of the procedure for judging the presence or absence of biosignals at the bedding state judgment control section 7. At the start of the procedure, 'biosignal is absent' is set. When data of Aa and $Aa_0$ are taken in, the biosignal intensity F is calculated using the equation (A). When the biosignal intensity F exceeds F (30), a judgment of 'biosignal is present' is given. When the biosignal intensity F is F (30) or lower, a judgment of 'biosignal is absent' is given.

When the biosignal intensity F exceeds F (30) to produce the judgment of 'biosignal is present,' the data of Aa and $Aa_0$ are taken in again and the calculation using the equation (A) is repeated. If the calculation gives the biosignal intensity F of F (20) or lower, the judgment of 'biosignal is absent' is given, and the same steps are repeated.

Thus, the value F (30) is used as a threshold for the biosignal intensity F in judging the presence or absence of biosignals. This threshold, however, may be changed according to differences in age, physical structure, or condition among individual subjects.

Figure 5:
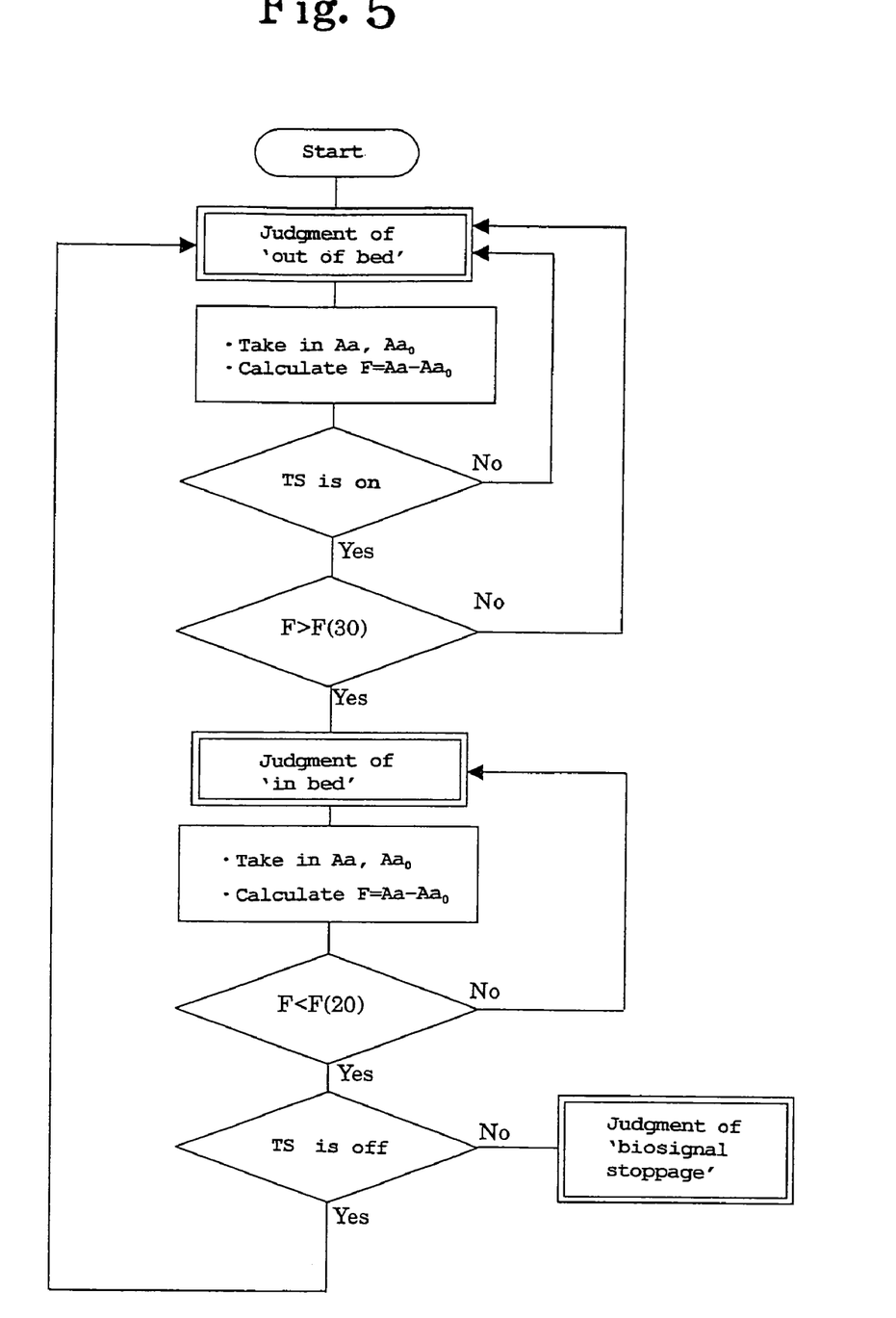
FIG. 5 is a flowchart of a procedure for judging a subject's being in or out of bed.

FIG. 5 is a flowchart of an example of the procedure for judging a subject's moving from in bed to out of bed or being in or out of bed, and/or the presence or absence of biosignals. In other words, the procedure is used to monitor the subject to see if he or she is on the bed or leaving the bed, or to see if on the bed, any accident, such as the stoppage of biosignals, is occurring.

At the start of the procedure, 'out of bed' is set. When data of Aa and $Aa_0$ are taken in, the biosignal intensity F is calculated using the equation (A). When the tape switch used as the non-bedding detecting sensor 11 is on and the biosignal intensity F is above F (30), it is confirmed that the subject is in the bed 8 and biosignals are detected, therefore, the judgment of 'in bed' is given.

When the presence of the subject in the bed is confirmed, the data of Aa and $Aa_0$ are taken in again and the calculation by the equation (A) is repeated.

If the calculation gives the biosignal intensity F of F (20) or lower, output from the non-bedding detecting sensor 11 is checked. When the output from the non-bedding detecting sensor 11 is not observed, it indicates that a given weight is not applied to the bed, which leads to a judgment that the subject is out of the bed. At this time, the procedure returns to the start of the flowchart. On the other hand, when the output from the non-bedding detecting sensor 11 is observed, it indicates that the biosignal intensity F is at a low level of F (20) or lower despite the fact that the subject is in the bed. This leads to a judgment of 'biosignal stoppage', that is, the abnormal state of the subject, at which an alarm is emitted from an alarm device 7 to report the abnormal state to the prescribed personnel, institution, or post.

Figure 7A:
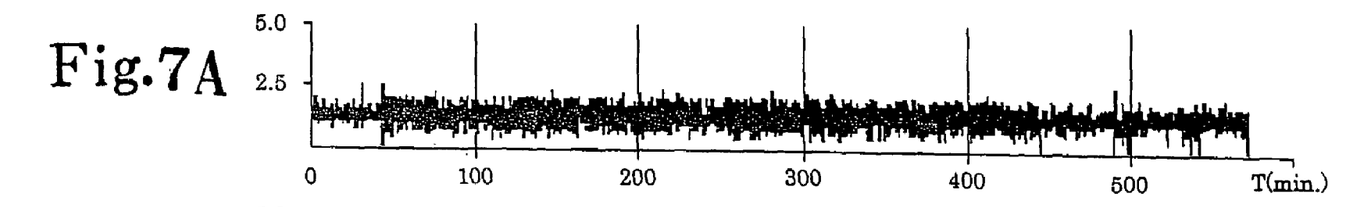
FIGS. 7A-7D are graphs showing biosignal output actually measured according to one embodiment.

FIGS. 7A-7D are graphs showing the biosignal output actually measured according to the biosignal intensity measuring method and the bedding state judging method. FIG. 7A shows the waveform of the AGC output of a noninvasive sensor signal.

Figure 7B:
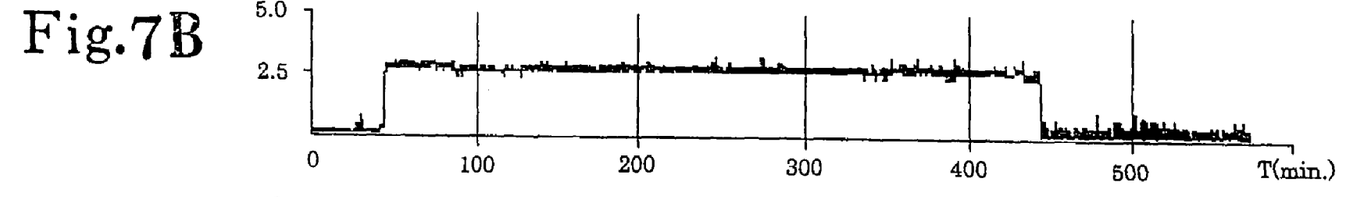
Figure 7C:
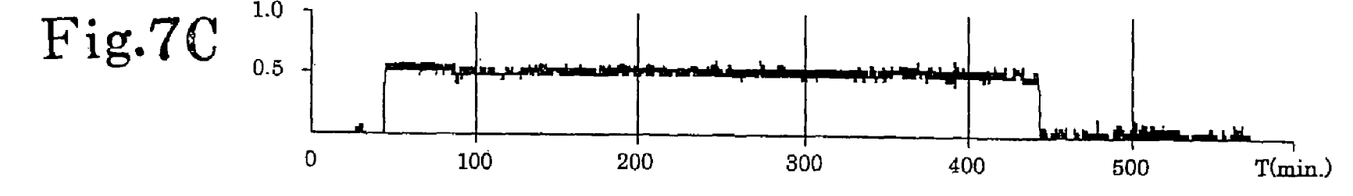

FIG. 7B is a graph showing the signal intensity Aa given by calculating the intensity of signals from the noninvasive sensor 1 at the signal intensity calculating section 4, where the signal intensity Aa is normalized to have a maximum value of one. FIG. 7C is a graph showing a signal from which the biosignal intensity Aao under a non-loaded condition is deducted.

Figure 7D:
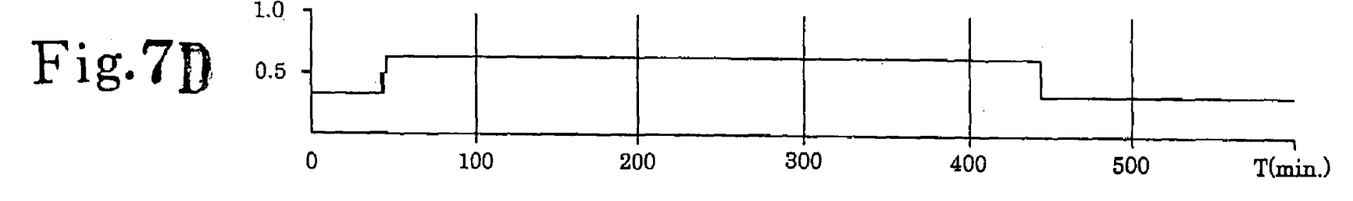

FIG. 7D represents a signal output for judging the presence or absence of biosignals, which is a result of a judgment made in accordance to the flowchart shown in FIG. 4. If the signal output reaches one, it is judged that biosignals are present. The signal output shown in FIG. 7D is combined with output from the non-bedding detecting sensor 11 for judgment about a subject's being in or out of bed and for monitoring of the abnormal state of the subject according to the flowchart shown in FIG. 5.

The method and apparatuses according to the described embodiments enable noninvasive monitoring of a subject's being in or out of bed, of the biosignal intensity, and of the presence or absence of body motion, such as tossing or turning. This makes it possible to detect the abnormal state of the subject, such as the stoppage of biosignals, and also to know the daily behavior of the subject, including a pattern of tossing or turning, getting in or out of bed, etc., by recording information of the subject constantly. As a result, checking the overall life pattern of the subject becomes possible. Such detected or checked information may be transmitted to subject's close relatives or family doctor in a remote location to help the receiver maintain the subject's health.

Also, according to the biosignal intensity measuring method, by using the noninvasive sensor as a detecting unit for detecting biosignals from the subject, the subject is freed from any physical burden in daily activity during the monitoring operation, so that the noninvasive sensor can be used without any concern. Additionally, the method includes a unit that reduces environmental noises not caused by the subject, which realizes accurate measuring of biosignal intensity.

Furthermore, the bedding state judging method and the bedding state judging apparatus, which includes the use of the biosignal intensity measuring method, enable the confirmation of a subject's being in or out of bed and monitoring of the subject to detect any abnormal state and thereby inform a medical professional or subject's family members of the abnormality.

If the subject is an elderly person, his or her family members do not have to visit the subject frequently to see if he or she is all right because the family members are assured that they are informed of any abnormality immediately upon occurrence. Further, the family members are provided with information of the subject's being in or out of bed as well. In a case of an elderly person living alone, monitoring information of the elderly person can be transmitted to a remote place using the method and apparatus as described, which makes remote monitoring of the person possible.

The method and apparatus are also applicable to institutions like hospitals or homes for the elderly, reducing the burden on nurses and the labor to patrol the bed areas.

As described above, the biosignal intensity measuring method, bedding state judging method, and bedding state monitor are useful, for example, in medical institutions, institutions for the elderly, hospices, and homes and are also good for use as a monitoring system and condition detecting system for the elderly.

The invention claimed is:

1. A biosignal intensity processing method to judge a bedding state of a subject, the method comprising:
   amplifying biosignals from a lying subject which have been detected by a non-invasive sensor and attenuating noises other than the biosignals detected by the non-invasive sensor via a signal amplifying/shaping means;
   subjecting the amplified biosignals to an automatic gain control (AGC) means which controls gain such that the amplified biosignals are processed to have sizes within a prescribed range; and
   calculating a biosignal intensity value by applying the controlled gain to a function that inversely relates the controlled gain with the biosignal intensity, such that the biosignal intensity is large when the controlled gain is small, and the biosignal intensity is small when the controlled gain is large.

2. The biosignal intensity processing method according to claim 1, wherein the signal amplifying/shaping means has a characteristic that reduces a signal level of heartbeat signals and pulse signals in a bandwidth other than the main bandwidth of the biosignals.

3. The biosignal intensity processing method according to claim 1, wherein the signal amplifying/shaping means has a band-pass filter that reduces a signal level of heartbeat signals and pulse signals in a bandwidth other than the main bandwidth of the biosignals.

4. The biosignal intensity processing method according to claim 1, wherein when the size of biosignals detected by the non-invasive sensor exceeds a prescribed range for more than a certain time, further including judging that a subject is making body motion.

5. A method for judging a bedding state of a subject, said method comprising:
   amplifying biosignals from a lying subject which have been detected by a non-invasive sensor and attenuating noises other than the biosignals detected by the non-invasive sensor via a signal amplifying/shaping means;
   processing the biosignals in an automatic gain control (AGC) means which controls gain such that the amplified biosignals are processed to acquire sizes within a prescribed range;
   calculating a biosignal intensity value by applying the controlled gain to a function that inversely relates the controlled gain with the biosignal intensity, such that the biosignal intensity is large when the controlled gain is small, and the biosignal intensity is small when the controlled gain is large;
   judging a bedding state of the subject using a lying-state detection sensor for detecting whether a subject is lying in bed, wherein when (1) the lying-state detection sensor detects the subject lying in bed and (2) when the calculated biosignal intensity exceeds a first predetermined intensity, judging that the subject is in bed, and otherwise judging that the subject is out of bed;
   determining whether a newly calculated biosignal intensity exceeds a second predetermined intensity; and
   judging that the subject is lying in bed in a normal condition when the newly calculated biosignal intensity exceeds the second predetermined intensity, judging that the subject is out of bed when the newly calculated biosignal intensity is less than or equal to the second predetermined intensity, and judging that the subject is in an abnormal condition when the newly calculated biosignal intensity is less than or equal to the second predetermined intensity and the lying-state detection sensor detects that the subject is lying in bed.

6. The method according to claim 5, wherein the signal amplifying/shaping means has a characteristic that reduces a signal level of heartbeat signals and pulse signals in a bandwidth other than the main bandwidth of the biosignals.

7. The method according to claim 5, wherein the signal amplifying/shaping means has a band-pass filter that reduces a signal level of heartbeat signals and pulse signals in a bandwidth other than the main bandwidth of the biosignals.

8. A bedding state monitoring device, comprising:
   a noninvasive sensor that detects biosignals emitted by a lying subject;
   a signal amplifying/shaping means for amplifying the biosignals detected by the non-invasive sensor, while attenuating noises other than the biosignals detected by the noninvasive sensor;
   a lying-state detecting sensor for detecting whether a subject is lying in bed;
   an automatic gain control (AGC) means that controls gain such that the amplified biosignals are processed to have sizes within a prescribed range;
   a biosignal intensity calculating means that calculates a biosignal intensity value by applying the controlled gain to a function that inversely relates the controlled gain with the biosignal intensity, such that the biosignal intensity is large when the controlled gain is small, and the biosignal intensity is small when the controlled gain is large.
   a judging means wherein, when the lying-state detecting sensor detects that the subject is lying in bed and when the calculated biosignal intensity exceeds a first predermined intensity, judges that the subject is in bed, and otherwise judges that the subject is out of bed; and
   wherein, when the lying-state detection sensor detects that the subject is lying in bed and when a newly calculated biosignal intensity exceeds a second predetermined intensity, the judging means judges that the subject is lying in bed in a normal condition, and when the newly calculated biosignal intensity is less than or equal to the second predetermined intensity and the lying-state detection sensor detects that the subject is not lying in bed, the judging means judges that the subject is out of bed: and when the newly calculated biosignal intensity is less than or equal to the second predetermined intensity and the lying-state detection sensor detects that the subject is lying in bed, the judging means judges that the subject is in an abnormal condition.

9. The bedding state monitoring device according to claim 8, wherein the signal amplifying/shaping means has a characteristic that reduces the intensity level of heartbeat signals and pulse signals in a bandwidth other than a main bandwidth of the signals.

10. The bedding state monitoring device according to claim 8, wherein the signal amplifying/shaping means has a band-pass filter that reduces an intensity level of heartbeat signals and pulse signals in a bandwidth other than a main bandwidth of the signals.

11. The bedding state monitoring device according to claim 8, further comprising a body motion detecting means that detects body motion from the output of the noninvasive sensor, wherein the bedding state judging means monitors the occurrence of the body motion using output from the body motion detecting means.

12. The bedding state monitoring device according to claim 11, wherein the body motion detecting means judges that a subject is making body motion when a size of output from the noninvasive sensor exceeds a prescribed range for more than a certain time.

13. The bedding state monitoring device according to claim 8, wherein the noninvasive sensor comprises a capacitor microphone for detecting micropressure, and a hollow, elastic tube or a hollow, elastic tube with an inserted core wire thinner than a hollowed part of the tube, the tube being connected to the microphone.

14. The bedding state monitoring device according to claim 8, wherein the lying-state detecting sensor is a sensor for detecting weight.

15. The bedding state monitoring device according to claim 8, wherein the lying-state detecting sensor is an infrared sensor.

16. A patient status sensing device, comprising:
  a pressure detecting element;
  a signal amplifying/shaping section, that removes noise from an output of the pressure detecting element;
  a gain control section that processes an output of the signal amplifying/shaping section by controlling gain so that the output of the signal amplifying/shaping section is processed into signals within a prescribed range;
  a body motion detecting calculating section; and
  a status judgment section that determines patient status based on inputs from the signal amplifying/shaping section, the body motion detecting calculating section, and the gain control section, where the input from the gain control section includes controlled gain.

17. The patient sensing device according to claim 16, further comprising an alarm device connected to the status judgment section.

18. The patient sensing device according to claim 16, further comprising an out-of-bed detecting sensor that provides another input into the status judgment section.

19. The patient sensing device according to claim 16, wherein the pressure detecting element comprises an elongated tube having a closed end at an end and a differential pressure sensor at the other end of the elongated tube.

20. The patient sensing device according to claim 19, wherein the elongated tube is arranged in a serpentine pattern between a patient and a surface upon which the patent lies.

* * * * *